(12) United States Patent
Ahmed et al.

(10) Patent No.: US 9,321,639 B2
(45) Date of Patent: Apr. 26, 2016

(54) PROCESS FOR METHANOL AND AMMONIA CO-PRODUCTION

(75) Inventors: Ijaz C. Ahmed, Riyadh (SA); Mubarak Bashir, Riyadh (SA)

(73) Assignee: SAUDI BASIC INDUSTRIES CORPORATION, Riyadh (SA)

( * ) Notice: Subject to any disclaimer, the term of this patent is extended or adjusted under 35 U.S.C. 154(b) by 134 days.

(21) Appl. No.: 13/391,433

(22) PCT Filed: Aug. 17, 2010

(86) PCT No.: PCT/EP2010/005114
§ 371 (c)(1), (2), (4) Date: Feb. 21, 2012

(87) PCT Pub. No.: WO2011/020618
PCT Pub. Date: Feb. 24, 2011

(65) Prior Publication Data
US 2012/0148472 A1   Jun. 14, 2012

(30) Foreign Application Priority Data

Aug. 20, 2009   (EP) .................................... 09075380

(51) Int. Cl.
*C01B 3/02*       (2006.01)
*C07C 29/151*     (2006.01)
(Continued)

(52) U.S. Cl.
CPC .............. *C01B 3/025* (2013.01); *C01C 1/0488* (2013.01); *C07C 29/1516* (2013.01);
(Continued)

(58) Field of Classification Search
CPC .................. C07C 29/1516; C07C 31/04; B01J 2219/00006; C01B 2203/0244; C01B 2203/061; C01B 2203/068; C01B 2203/1235; C01B 2203/1258; C01B 3/025; C01C 1/0488
USPC .......................................... 422/148; 423/359
See application file for complete search history.

(56) References Cited

U.S. PATENT DOCUMENTS 2,014,757 A   9/1935   Blondelle
3,598,527 A   8/1971   Quartulli et al.
(Continued)

FOREIGN PATENT DOCUMENTS

DE   3336649 A1   4/1985
DE   3443017 A1   6/1985
(Continued)

OTHER PUBLICATIONS

Japanese Patent No. 06234517 (A); Publication Date: Aug. 23, 1994; Abstract Only; 1 Page.
(Continued)

*Primary Examiner* — Fereydoun G Sajjadi
*Assistant Examiner* — Amy C Bonaparte
(74) *Attorney, Agent, or Firm* — Cantor Colburn LLP

(57) ABSTRACT

This invention relates to a process for co-producing methanol and ammonia, wherein a syngas mixture consisting essentially of carbon monoxide (CO), carbon dioxide ($CO_2$) and hydrogen ($H_2$) is first partially reacted in a methanol once-through reactor, unreacted syngas is divided into a first and a second stream, the first stream is purified and fed to an ammonia synthesis section, and the second stream is fed to a methanol synthesis and purification section. With this process it is possible to produce methanol and ammonia at very high capacities in an integrated single process, applying unit operations not exceeding current practical capacity limitations. For example, the process allows production of 8000 mtpd of methanol and 2000 mtpd of ammonia starting from natural gas and air. The process further shows a balanced production of ammonia and carbon dioxide, thus allowing co-production of urea also to be integrated.

18 Claims, 1 Drawing Sheet

(51) Int. Cl.
*C07C 31/04* (2006.01)
*C01C 1/04* (2006.01)

(52) U.S. Cl.
CPC ............... *B01J 2219/00006* (2013.01); *C01B 2203/0244* (2013.01); *C01B 2203/061* (2013.01); *C01B 2203/068* (2013.01); *C01B 2203/1235* (2013.01); *C01B 2203/1258* (2013.01)

(56) References Cited

U.S. PATENT DOCUMENTS

| | | | |
|---|---|---|---|
| 3,615,200 | A | 10/1971 | Koneki |
| 3,872,025 | A | 3/1975 | Singleton |
| 3,957,449 | A * | 5/1976 | Ciechowski ............... 422/203 |
| 4,013,454 | A | 3/1977 | Jordan |
| 4,110,359 | A | 8/1978 | Marion |
| 4,311,671 | A | 1/1982 | Notman |
| 4,315,900 | A | 2/1982 | Nozawa et al. |
| 4,327,068 | A | 4/1982 | Lagana et al. |
| 4,367,206 | A | 1/1983 | Pinto |
| 4,810,417 | A | 3/1989 | Diemer et al. |
| 4,886,651 | A | 12/1989 | Patel et al. |
| 4,946,477 | A * | 8/1990 | Perka et al. ............... 48/197 R |
| 5,180,570 | A | 1/1993 | Lee et al. |
| 5,211,880 | A | 5/1993 | Primdahl et al. |
| 6,106,793 | A | 8/2000 | Badano et al. |
| 6,333,014 | B1 * | 12/2001 | Filippi ............... 423/359 |
| 7,521,483 | B2 | 4/2009 | Davey et al. |
| 2007/0142482 | A1 * | 6/2007 | Jung et al. ............... 518/726 |
| 2007/0161716 | A1 | 7/2007 | Xie et al. |
| 2007/0225384 | A1 * | 9/2007 | Thiebaut ............... 518/705 |
| 2007/0244208 | A1 * | 10/2007 | Shulenberger et al. ...... 518/726 |
| 2007/0299144 | A1 | 12/2007 | Davey et al. |
| 2008/0039625 | A1 * | 2/2008 | Lautens et al. ............... 544/363 |
| 2009/0018372 | A1 * | 1/2009 | Tirmizi et al. ............... 568/916 |
| 2009/0292148 | A1 * | 11/2009 | Gracey et al. ............... 568/955 |

FOREIGN PATENT DOCUMENTS

| | | | |
|---|---|---|---|
| EP | 0112613 | B1 | 7/1984 |
| EP | 0139423 | A2 | 5/1985 |
| GB | 366268 | A | 2/1932 |
| GB | 715881 | A | 9/1954 |
| GB | 1270756 | A | 4/1972 |
| GB | 1314984 | A | 4/1973 |
| GB | 1502190 | A | 2/1978 |
| GB | 306512 | A | 7/1980 |
| GB | 2084973 | A | 4/1982 |
| GB | 2252317 | A | 8/1992 |
| JP | 55067501 | A | 5/1980 |
| JP | 55162422 | A | 12/1980 |
| JP | 06234517 | A | 8/1994 |
| JP | 2000063115 | A | 2/2000 |
| JP | 2002161303 | A | 6/2002 |
| WO | 2006114108 | A1 | 11/2006 |
| WO | 2008122399 | A1 | 10/2008 |

OTHER PUBLICATIONS

Japanese Patent No. 2000-063115 (A); Publication Date: Feb. 29, 2000; Abstract Only; 1 Page.
International Publication No. 2006114108 (A1); Publication Date: Nov. 2, 2006; Abstract Only; 1 Page.
German Patent No. 3336649 (A1); Publication Date: Apr. 25, 1985; Abstract Only; 1 Page.
German Patent No. 3443017 (A1); Publication Date: Jun. 5, 1985; Abstract Only; 1 Page.
Japanese Patent No. 55067501 (A); Publication Date: May 21, 1980; Abstract Only; 1 Page.
"Ammonia"; Kirk-Othmer Encyclopedia of Chemical Technology; Published by Wiley InterScience; DOI: 10.1002/0471238961.0113131503262116.a01_pub2; Available Online: Oct. 18, 2001; Accessed: Jan. 14, 2010; 22 Pages.
European Fertilizer Manufacturers' Associate (EFMA); "Best Available Techniques for Pollution Prevention and Control in the European Fertilizer Industry"; Booklet No. 1 of 8: Production of Ammonia; 2008; 40 Pages.
Extended European Search Report; European Application No. 09075380.7; Date of Mailing: Jan. 12, 2010; 5 Pages.
"Methanol"; Kirk-Othmer Encyclopedia of Chemical Technology; Published by Wiley InterScience; DOI: 10.1002/0471238961.1305200805140712.a01_pub2; Available Online: Feb. 18, 2005; Accessed: Jan. 14, 2010; 14 Pages.
P.F. van den Oosterkamp; "Synthesis Gas Generation: Industrial"; Encyclopedia of Catalysis; Published by John Wiley & Sons; DOI: 10.1002/0471227617.eoc196; Available Online: Dec. 13, 2002.
International Search Report; International Application No. PCT/EP2010/005114; International Filing Date: Aug. 17, 2010; Date of Mailing: Sep. 29, 2010; 6 Pages.
Written Opinion of the International Searching Authority; International Application No. PCT/EP2010/005114; International Filing Date: Aug. 17, 2010; Date of Mailing: Sep. 29, 2010; 7 Pages.
Udesen; "An Integrated Approach to Ammonia Production; Haldor Topsoe A/S"; Denmark; 19th AFA International Technical Conference; Doha Qatar; Apr. 18, 2006-Apr. 20, 2006.
Waller et al.; "Methanol Technology Developments for the New Millennium"; Applied Catalysis A: General; vol. 221; 2001; pp. 275-282.
Japanese Patent No. 2002161303; Date of Publication: Jun. 4, 2002; Abstract Only, 2 pages.

* cited by examiner

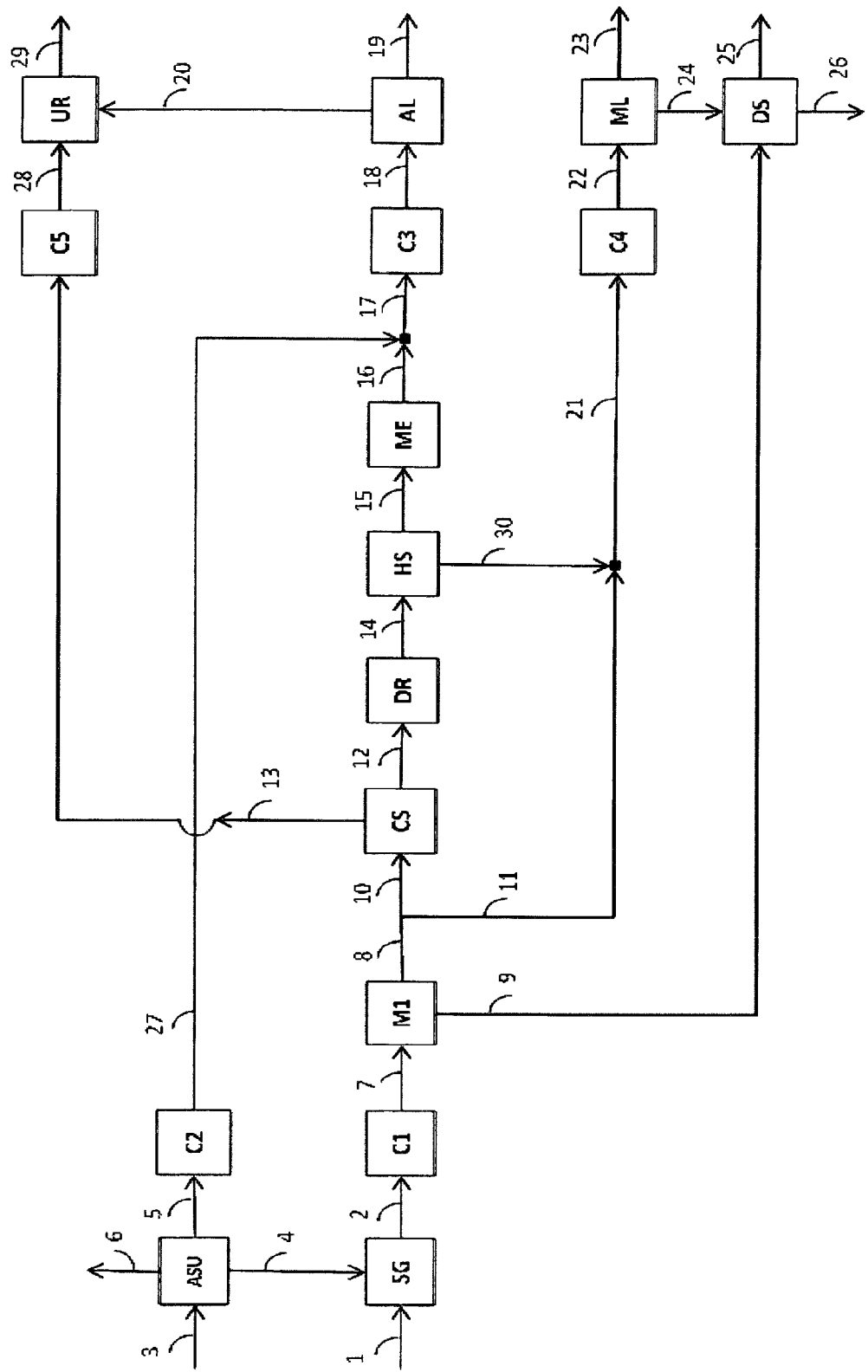

PROCESS FOR METHANOL AND AMMONIA CO-PRODUCTION

CROSS REFERENCE TO RELATED APPLICATIONS

This application is a 371 of International Application No. PCT/EP2010/005114, filed Aug. 17, 2010, which claims priority to European Application No. 09075380.7, filed Aug. 20, 2009, both of which are hereby incorporated by reference in its entirety.

TECHNICAL FIELD

The invention relates to an integrated process for co-producing methanol and ammonia from syngas, more specifically to a process of co-producing methanol and ammonia from a hydrocarbon feedstock and air. The invention further relates to an integrated process for co-producing methanol and urea, more specifically to a process of co-producing methanol and urea from a hydrocarbon feedstock and air.

BACKGROUND

Such a process is known from patent publication U.S. Pat. No. 7,521,483 B2. This document describes a process for co-producing methanol and ammonia from natural gas and air, comprising the steps of i. feeding air to an air separation section to make an oxygen ($O_2$) and a nitrogen ($N_2$) stream;
ii. reforming desulphurised natural gas with the $O_2$ stream and steam in a combined reforming section to make a syngas mixture comprising carbon monoxide (CO), carbon dioxide ($CO_2$), steam ($H_2O$) and hydrogen ($H_2$);
iii. Dividing the syngas mixture into a first and a second syngas stream;
iv. Feeding the first syngas stream to a syngas purification section to make a $CO_2$ and a $H_2$ stream;
v. Dividing the $H_2$ stream into a first and a second stream;
vi. Purifying the first $H_2$ stream with the $N_2$ stream to make a pure $H_2/N_2$ stream;
vii. Feeding the $H_2/N_2$ stream to an ammonia synthesis section to make an ammonia stream;
viii. Feeding the second $H_2$ stream and the second syngas stream to a methanol loop reactor to make a methanol-containing mixture;
ix. Separating crude methanol from the methanol-containing mixture and recycling the remaining gas to the methanol loop reactor;
x. Feeding the crude methanol to a methanol purification section to result in a methanol stream.

It is indicated that this process enables production of up to 5000 mtpd (metric ton per day) of methanol combined with up to 4000 mtpd of ammonia. The process may further comprise reacting the $CO_2$ and $NH_3$ formed into up to 6800 mtpd of urea.

Methanol is one of the most important chemical raw materials; most of the methanol produced is used as a starting material or solvent for synthesis, whereas its use in the fuel and energy sector is expected to increase significantly. Since the 1960's, methanol synthesis from sulphur-free synthesis gas (syngas) with Cu-based catalysts has become the major route, as it can be operated at fairly mild reaction conditions. An overview of methanol processes can be found for example in the chapter "Methanol" in "Kirk-Othmer Encyclopedia of Chemical Technology" (Wiley InterScience; posted on-line 2005/02/18, available via DOI: 10.1002/0471238961.1305200805140712.a01.pub2).

Ammonia is another major chemical raw material, which is used for making urea and other fertilizers, and various chemicals like caprolactam and melamine. It is produced worldwide from nitrogen and hydrogen, typically the hydrogen is obtained via steam reforming of natural gas (or other hydrocarbon feedstock). An overview of ammonia processes can be found for example in the chapter "Ammonia" in "Kirk-Othmer Encyclopedia of Chemical Technology" (Wiley InterScience; posted on-line 2001/10/18, available via DOI: 10.1002/0471238961.0113131503262116.a01.pub2).

For both methanol and ammonia production, it is advantageous—from an economical viewpoint—to develop single line plants with capacity as high as possible. Manufacturing capacity of a single line plant, incorporating only one operating unit or device for each relevant reaction or separation step, is typically limited for technological and economical reasons by a maximum capacity of one or more of its units. Reliability of all units is paramount, as minimizing downtime is a prerequisite for economical operation. For example, a single state-of-the-art air separation unit (abbreviated as ASU) is considered to produce at most about 4000 mtpd (or 5200 kmol/h) of oxygen. Such ASU subsequently limits production capacity of reactors using oxygen as reactant; for example of an auto-thermal reforming (ATR) unit producing syngas from natural gas, steam and oxygen (an ATR is basically a combination of a steam methane reformer (SMR) and a partial oxidation (POX) reactor). Limitations in the maximum size of a SMR unit, on the other hand, lay in the number of reactor tubes. About 1000 tubes is considered to be the maximum for a single unit operation, otherwise it will not be possible to control uniform distribution of gasses and thus heat transfer to all tubes. Further capacity limitation results from a certain maximum amount of energy that can be transferred to the tubes. It is thus estimated that a technically and economically feasible SMR reactor of maximum capacity is currently characterized by a maximum reforming heat load of about 1150 GJ/h. Methanol is typically produced on large scale in a so-called loop reactor, because conversion of syngas into methanol is relatively low. This means that an enormous volume of gas needs to be handled and recycled. For this reason, methanol loop reactors have currently a maximum capacity of 5000-6000 mtpd of methanol.

Integration of methanol and ammonia plants offers further options to reduce costs and boost capacity, by sharing unit operations, internally recycling material streams and re-use of energy (heat). In older processes, a syngas containing carbon oxides (CO and $CO_2$), hydrogen and nitrogen is made, and converted partially to methanol in a methanol loop reactor, methanol is separated from the effluent, and unreacted gas is purified and then fed to an ammonia reactor downstream. An example hereof is given in U.S. Pat. No. 4,367,206, proposing an improvement of such sequential methanol and ammonia co-production using syngas containing carbon oxides, hydrogen and nitrogen as feed, by carrying out the methanol synthesis in two stages, with and without water being present. In DE 3336649 A1 sequential co-production of methanol and ammonia from methane and air is described, wherein the hydrogen/nitrogen ammonia synthesis gas stream is made by reacting excess hydrogen, separated from effluent of the methanol loop reactor, with air.

An integrated process for co-producing methanol and ammonia is also disclosed in U.S. Pat. No. 6,333,014 B1, which process contains the steps of i. Reforming desulphurised hydrocarbon with steam and air in primary and secondary reformer to make a syngas mixture;

ii. Dividing the syngas mixture into a first and a second syngas stream;

iii. Cooling the first syngas stream to remove a water stream, and feeding remaining syngas to a methanol once-through reactor to make a methanol-containing mixture;

iv. Separating the methanol-containing mixture into crude methanol and methanol-free gas;

v. Feeding the second syngas stream to a high-temperature CO convertor;

vi. Feeding effluent of the high-temperature CO convertor, the methanol-free gas and the water stream to a low-temperature CO convertor;

vii. Feeding effluent of the low-temperature CO convertor to an ammonia synthesis section to make ammonia.

U.S. Pat. No. 5,180,570 also describes an integrated process for co-producing methanol and ammonia from a hydrocarbon feedstock and air, which comprises the steps of i. separating air into substantially pure $O_2$ and $N_2$ streams;

ii. reforming desulphurised hydrocarbon with steam and $O_2$ in a combined reforming section to make a methanol syngas stream;

iii. Feeding the methanol syngas stream to a methanol loop reactor to make a methanol-containing mixture;

iv. Separating crude methanol from the methanol-containing mixture, and recycling a first part of the remaining gas to the methanol loop reactor;

v. Purifying a second part of the remaining gas and mixing it with $N_2$ to make a ammonia syngas stream;

vi. Feeding the ammonia syngas stream to an ammonia synthesis section to make ammonia.

Considering the increasing demand for fuel and energy, there is a need in industry for ever larger and more efficient methanol and ammonia plants. Presently operated integrated production processes for making methanol and ammonia from hydrocarbon feedstock typically use methanol loop reactors, which have maximum capacity on the order of 5000 mtpd, and need to handle gas volumes about 5 times as much for recycling effluent gas.

There is a continuous need in the industry for a single-line process for making methanol and ammonia in an efficient and economical way, applying unit operations not exceeding current practical capacity limitations (as described above).

SUMMARY

This object is achieved according to the present invention as defined in the description and claims, more specifically with a process for co-producing methanol and ammonia, wherein a syngas mixture consisting essentially of carbon monoxide (CO), carbon dioxide ($CO_2$) and hydrogen ($H_2$) is first partially reacted in a methanol once-through reactor, unreacted syngas is divided into a first and a second stream, the first stream is purified and fed to an ammonia synthesis section, and the second stream is fed to a methanol synthesis and purification section.

BRIEF DESCRIPTION OF THE DRAWING

FIG. 1 is a schematic of a simplified block scheme of an embodiment of a process for co-producing methanol and ammonia.

DETAILED DESCRIPTION

With the process according to the invention it is possible to produce methanol and ammonia at very high capacities in an integrated single process. For example, the process allows production of 8000 mtpd of methanol and 2000 mtpd of ammonia starting from natural gas and air, and applying a methanol loop reactor well below current maximum capacity limits. The process further shows a balanced production of ammonia and carbon dioxide, thus allowing co-production of urea also to be integrated.

In the process according to the invention for co-producing methanol and ammonia, a syngas mixture consisting essentially of carbon monoxide (CO), carbon dioxide ($CO_2$) and hydrogen ($H_2$) is first partially reacted into methanol. Syngas is generally defined as a gaseous mixture made by reforming a hydrocarbon feedstock, and contains hydrogen ($H_2$) and carbon monoxide (CO), and optionally other gas components like carbon dioxide ($CO_2$), water ($H_2O$), methane ($CH_4$), and nitrogen ($N_2$). Within the context of the present invention, a syngas mixture consisting essentially of carbon monoxide (CO), carbon dioxide ($CO_2$) and hydrogen ($H_2$) is understood to contain only minor amounts of other components; i.e. at such levels that the methanol synthesis reaction is not negatively affected. For example, the water content is below the maximum amounts generally accepted in a feed for methanol production. Typically, syngas as obtained from a reforming section is cooled and condensed to essentially remove the water present. Nitrogen content of the syngas is also low, as preferably no air is added during the preceding reforming process, but rather only steam and oxygen.

The composition of synthesis gas, and thus its suitability for use for e.g. methanol production, is characterized mainly by its hydrogen and carbon monoxide content; generally presented by the so-called stoichiometric number (SN), which is defined as $$SN=([H_2]-[CO_2])/([CO]+[CO_2])$$

wherein the concentrations of components are expressed in vol % or mol %.

The value of SN is dependent on the feedstock and the reforming process used to make syngas. An overview of different suitable reforming technologies and their advantages and limitations is for example given by P. F. van den Oosterkamp in chapter "Synthesis Gas Generation: Industrial" of the "Encyclopedia of Catalysis" (John Wiley & Sons; posted on-line 2002/12/13, available via DOI: 10.1002/0471227617.eoc196).

For methanol synthesis a syngas mixture is used that preferably has a SN of 1.9-2.5, more preferably SN is 1.9-2.3, 2.0-2.2, or 2.0-2.1. For co-producing methanol and ammonia the SN of the syngas may be somewhat higher than for methanol only, excess of hydrogen will be used in the ammonia synthesis section; but preferably composition is optimised for methanol conversion.

In the process according to the invention the syngas mixture can have been made or can be made with any known process that results in the desired composition and quantities of syngas. Preferably, the syngas is made with a combined reforming process, i.e. with a process wherein a combination of different reforming reactors is used. Generally, reforming reactors are classified as being one of the following types. Conventionally, reforming of methane-rich feedstock is done in a steam methane reformer (hereinafter abbreviated as SMR) by first mixing feedstock with steam and then feeding to a combustion-type (also called fired) reactor. A second type is a heat-exchange type steam reforming reactor that is heated with hot gasses produced elsewhere in the process (also called gas heated reformer, hereinafter abbreviated as GHR). An auto-thermal reformer (abbreviated as ATR) is a reforming unit wherein the gasses undergo a (catalytic) partial oxidation reaction with oxygen under essentially adiabatic conditions in addition to further reaction with steam, the excess heat generated by the exothermic oxidation reactions being used to supply heat for the endothermic steam reforming reaction. In a partial oxidation reactor (POX) feedstock is mainly reformed by thermal partial oxidation and steam reforming. If a feedstock is used that is rich in higher hydrocarbons, like naphtha, the feedstock is typically first treated in a so-called pre-reforming step, in order to convert the heavy hydrocarbons in the feed into methane, hydrogen and carbon oxides. Such a pre-reformer is typically operated adiabatically, and is generally referred to as an adiabatic pre-reformer (APR).

Suitable examples of reforming processes are known from for example the above reference, from WO 2008/122399 A1, and from the documents cited therein.

Preferably, the process according to the invention further comprises a combined reforming section, wherein a desulphurised hydrocarbon feedstock is reformed with oxygen and steam. The inventive process is distinguished from prior art processes a.o. in that all syngas produced with specified composition is first fed to a methanol reactor.

In a preferred way of operating the process according to the invention syngas is made with a combined reforming process as described in WO 2008/122399 A1, wherein a desulphurised methane-rich feedstock is mixed with steam and passed through an adiabatic pre-reformer (APR), and wherein pre-reformed gas from the APR is divided into three streams that are fed to a steam methane reformer (SMR), a gas heated reformer (GHR) and—together with oxygen—to an autothermal reformer (ATR), which 3 reforming reactors are operated in parallel.

In a further preferred way of operating the process according to the invention, syngas is made with a combined reforming process from a desulphurised gaseous hydrocarbon feedstock, wherein the feedstock is divided into a first and a second feedstock stream, the first feedstock stream is mixed with steam and fed to a gas heated reformer (GHR) and a steam methane reformer (SMR) operated in series, and the second feedstock stream is mixed with reformed gas coming from the SMR and then fed with oxygen to a partial oxidation reformer (POX).

Because the syngas used as feed for partially reacting into methanol contains only low levels of nitrogen, preferably oxygen is used for partial oxidation during the reforming process. For this reason, the process according to the invention preferably further comprises an air separation section, wherein pure oxygen and nitrogen streams are made by separating from air, which oxygen and nitrogen are applied for making syngas and ammonia in the process, respectively. Any conventional air separation unit (ASU) able to deliver the needed quantities can be applied in the process according to the invention.

In the process of the present invention any hydrocarbon feedstock that is gaseous at reforming conditions can be used, like a hydrocarbon mixture having H/C ratio of about 2 to 4. Suitable examples include hydrocarbons like methane, ethane, methane-rich mixtures, or light naphtha (mixture of mainly C5-C9 paraffin compounds).

A suitable example of a methane-rich feedstock is natural gas, as obtained from gas or oil fields. The primary component of natural gas is methane, which is generally present in amounts of from 80 to 97 mol %. Natural gas also contains other gaseous hydrocarbons such as ethane, typically from about 3 to 15 mol %, propane, butane and small amounts of higher hydrocarbons (generally less than 5 mol % in total), as well as sulphur-containing gases, like hydrogen sulphide, in varying amounts. Further minor (or even trace) amounts of nitrogen, helium, carbon dioxide, water, odorants, and metals like mercury can also be present. The exact composition of natural gas varies with its source.

Organo-sulphur compounds and hydrogen sulphide ($H_2S$) are common contaminants of hydrocarbons from natural sources, which should be removed prior to use of hydrocarbon gas as a feedstock in the present process, to avoid poisoning of reforming catalysts. Desulphurisation can be done with conventional techniques. In a suitable process, organo-sulphur compounds in the feedstock are converted to $H_2S$ with a hydrogen-rich stream (for example a purge stream from a methanol synthesis loop), which is subsequently removed by passing over a suitable absorbent, to result in a sulphur content of the desulphurised gaseous feed of typically below 1 ppm.

Preferably, the desulphurised hydrocarbon feedstock in the process according to the invention is a methane-rich feedstock that contains as least 75 mol % of methane (based on total hydrocarbon content of the feedstock), more preferably at least 80, 85, 90, 92, 94 even at least 96 mol % of methane.

In the process according to the invention for co-producing methanol and ammonia, a syngas mixture is first partially reacted in a methanol once-through reactor. Within the context of this invention, a 'methanol once-through reactor' is understood to mean a reaction section wherein syngas is partly reacted into methanol, and unreacted effluents (syngas) are not recycled to the reactor. Such reactor is thus different from a 'methanol loop reactor', which is a reaction section wherein feed gas is partly reacted into methanol, and unreacted effluents are continuously separated and recycled to the reactor. In a loop reactor section significantly higher volumes of gas thus need to be handled, e.g. gas flow rates about 4-6 times higher compared to a once-through reactor, and accordingly larger reactor and associated equipment (heat-exchangers, separator, compressor, etc) are needed. Investment and operating costs for a once-through methanol reactor system are thus markedly lower than for a methanol loop reactor handling the same amount of feed gas. The process according to the invention also applies a methanol loop reactor section downstream, but of relatively small size.

A further advantage of the process according to the invention is that the concentration of carbon oxides is relatively high in the syngas feed, resulting in relatively high conversion to methanol. Syngas conversion to methanol in the once-through methanol reactor may be as high as 15, 20, 25, 30, 35, 40, 45 or even 50% in the process according to the invention.

In the process according to the invention syngas is first partially reacted in a methanol once-through reactor, whereafter unreacted syngas is divided into a first and a second stream, the first stream is then purified and fed to an ammonia synthesis section, and the second stream is fed to a methanol synthesis and purification section. The ammonia synthesis section, and the methanol synthesis and purification section can be any conventional system typically applying loop reactors and ammonia respectively methanol separators, and operated at conditions as known to a skilled person, for example from the general references given above. Such systems will therefore not be further described in detail.

The volume ratio of the first to the second stream of unreacted syngas is dependent on conversion to methanol, initial composition of the syngas and desired amounts of methanol and ammonia to be made, and can vary from about 50/50 to about 80/20. Preferably, the first and the second stream are divided in a ratio of from about 55/45 to 77/23 or from about 60/40 to 75/25, more preferably from 65/35 to 73/27. In a preferred embodiment the ratio is about 70/30.

The invention more specifically relates to a process for co-producing methanol and ammonia, comprising the steps of
a) Feeding a syngas mixture consisting essentially of CO, $CO_2$ and $H_2$ to a methanol once-through reactor to make a methanol/syngas mixture;
b) Separating the mixture of step a) into crude methanol and unreacted syngas;
c) Dividing the unreacted syngas of step b) into a first and a second stream;
d) Feeding the first stream of step c) to a syngas purification section to make a CO, a $CO_2$ and a $H_2$ stream;
e) Feeding the $H_2$ stream of step d) together with a $N_2$ stream to an ammonia synthesis section to make an ammonia stream;
f) Feeding the second stream of step c) and the CO stream of step d) to a methanol loop reactor to make a methanol-containing mixture;
g) Separating crude methanol from the methanol-containing mixture and recycling the remaining gas to step f);
h) Feeding the crude methanol from step b) and from step g) to a methanol purification section to result in a methanol stream.

Preferably, the process according to the invention co-produces methanol and ammonia from a methane-rich feedstock and air, and comprises the steps of
a") Feeding air to an air separation section to make an O2 and a N2 stream;
a') Reforming a desulphurised hydrocarbon feedstock with O2 from step a") and steam in a combined reforming section to make a syngas mixture consisting essentially of CO, CO2 and H2;
a) Feeding the syngas mixture of step a') to a methanol once-through reactor to make a methanol/syngas mixture;
b) Separating the mixture of step a) into crude methanol and unreacted syngas;
c) Dividing the unreacted syngas of step b) into a first and a second stream;
d) Feeding the first stream of step c) to a syngas purification section to make a CO, a CO2 and a H2 stream;
e) Feeding the H2 stream of step d) together with the N2 stream of step a") to an ammonia synthesis section to make an ammonia stream;
f) Feeding the second stream of step c) and the CO stream of step d) to a methanol loop reactor to make a methanol-containing mixture;
g) Separating crude methanol from the methanol-containing mixture and recycling the remaining gas to step f);
h) Feeding the crude methanol from step b) and from step g) to a methanol purification section to result in a methanol stream.

The invention further relates to an integrated process for co-producing methanol and urea according to the process as described, further comprising a subsequent step of making urea in a urea synthesis section from the $CO_2$ and $NH_3$ formed in the process. As urea synthesis section any urea production technology, equipment and process conditions as known in the art can be used.

In these processes according to the invention, preferred steps and options are those as already described in the above. The process of the invention will be discussed in more detail using an embodiment represented by the simplified block scheme as depicted in FIG. 1. In this FIGURE and in the following the symbols within the blocks have following meaning:
ASU Air separation unit
SG Syngas generation section
M1 Methanol once-through reactor section
CS Carbon dioxide separation unit
DR Dryer unit
HS Hydrogen separation unit
ME Methanator unit
AL Ammonia synthesis section
ML Methanol loop reactor section
DS Methanol distillation unit
UR Urea synthesis section
C1-C5 Compressor units 1-5.

The numbers used for the various process streams are further elucidated in the text below. The indicated pressures and temperatures are estimates for this embodiment; and are not limiting as alternative schemes and conditions may be applied as well.

In this scheme the ambient air feed stream 3 is separated in the ASU into essentially pure oxygen stream 4 (of at least 99.8% purity; typically compressed to e.g. 3-5 MPa), essentially pure nitrogen stream 5 (less than 5 ppm of impurities like $O_2$ and Ar; atmospheric), and a purge stream 6 containing a.o. nitrogen and argon. Nitrogen stream 5 is compressed in C2 to stream 27 (about 4-6 MPa; 140-170° C.) for use in the ammonia section.

Hydrocarbon feed 1 is reformed in the combined reforming section SG with oxygen stream 4 and steam (not shown) into a syngas mixture, which is cooled and condensed water is removed. Resulting stream 2 (about 3-4 MPa; 35-45° C.) is compressed in C1 to stream 7 (about 7-9 MPa; 90-120° C.). The entire amount of synthesis gas stream 7 is then fed to M1, operated at 7-8 MPa and at temperature of about 220-250° C. After passing the reactor crude methanol is removed, and fed as stream 9 (about 3-4 MPa; 40-50° C.) for purification in unit DS. With this arrangement about 3000-5000 mtpd of methanol is produced in section M1.

The remaining unreacted gas stream 8 (volume about 40-45% reduced vs 7) is then split at a ratio of about 70/30, but depending on desired ammonia/methanol product distribution, into stream 10 and stream 11 (both at about 6-8 MPa; 45-55° C.) for further methanol and ammonia production.

Stream 11 is mixed with CO-enriched stream 30 (about 6-7 MPa; 20-30° C.) from cryogenic hydrogen separation unit HS to make combined stream 21 (about 6-7 MPa; 40-45° C.) and further compressed in C4 to stream 22 (about 9-11 MPa; 80-100° C.), which is fed to conventional size methanol loop reactor ML, operated at about 8-10 MPa and 220-250° C. Condensed crude methanol stream 24 from ML (about 3-4 MPa; 40-45° C.) is then sent for purification in methanol distillation unit DS, together with stream 9. A small purge gas stream from unit DS, originating from flashing of high pressure crude methanol streams 9 and 24 is not shown in the scheme. Unreacted gas is recompressed and recycled to the loop reactor ML (not shown); a purge stream 23 (about 0.3-0.5 MPa; 40-50° C.) is used as fuel within the process. Methanol product is obtained as stream 26; stream 25 represents waste water.

In order to simplify the scheme, scrubbing water streams used for removing unreacted gasses from methanol with water in units M1 and ML are not shown.

The other divided stream 10 is further processed for ammonia synthesis. First carbon dioxide content is reduced in a conventional $CO_2$ separation section CS, which can be e.g. a MDEA, MEA, Benfield, Catacarb or Rectisol unit; resulting in substantially $CO_2$-free stream 12 (about 7-8 MPa; 40-45° C.) and $CO_2$ stream 13 (atmospheric). Stream 12 is subsequently passed through molecular sieve drying unit DR at about 6.5-7.5 MPa to result in substantially $CO_2$- and $H_2O$-free stream 14 (about 6.5-7.5 MPa; 40-50° C.) before it enters hydrogen separation unit HS, which is cryogenically operated at about −205 to −210° C. by expanding to a pressure of about 4-5 MPa. The resulting hydrogen stream 15 (about 4-5 MPa; 20-30° C.) contains still about 1 vol % CO, and is then passed through methanator unit ME, operated at about 2.5-5.0 MPa and 275-375° C., to give stream 16 (about 4-4.5 MPa; 90-100° C.) containing less than 10 ppm of carbon oxides. CO separated as stream 30 is preferably used to increase amount of methanol by mixing with stream 11.

Stream 16 is mixed with the required amount of nitrogen of stream 27 to give mixed stream 17 (about 4-5 MPa; 105-115° C.) containing hydrogen and nitrogen at 3/1 ratio; which is compressed in C3 to give stream 18 (about 15-16 MPa; 110-130° C.). Stream 18 is then fed as make-up gas to a loop in ammonia synthesis section AL, which reactor is operated at about 15-20 MPa and 350-450° C. A small purge stream 19 (about 0.3-0.5 MPa; 20-30° C.) is used as fuel within the process Ammonia product is obtained as stream 20, typically at 2-3 MPa and 40-50° C.

In a further preferred embodiment, $CO_2$ stream 13 is sent to urea synthesis section UR, after compression to about 16-20 MPa and 100-150° C. in unit C5, with the desired amount of ammonia via stream 20, to result in urea product 29 (in prilled or granular form).

The invention therefore also relates to an integrated production plant that is suitable for making methanol and ammonia from syngas with the process of the invention, comprising a methanol once-through reactor, a methanol loop reactor, a methanol purification section, a syngas purification section, and an ammonia synthesis section.

The invention further relates to an integrated production plant suitable for making methanol and ammonia from a methane-rich feedstock and air with the process according to the invention, comprising a combined reforming section, an air-separation section, a methanol once-through reactor, a methanol loop reactor, a methanol purification section, a syngas purification section, and an ammonia synthesis section.

The invention further relates to an integrated production plant suited for making methanol and urea from syngas applying the process of the invention, comprising a methanol once-through reactor, a methanol loop reactor, a methanol purification section, a syngas purification section, an ammonia synthesis section, and a urea synthesis section; as well as to an integrated production plant for making methanol and urea from a methane-rich feedstock and air applying the process of the invention, comprising a combined reforming section, an air-separation section, a methanol once-through reactor, a methanol loop reactor, a methanol purification section, a syngas purification section, an ammonia synthesis section, and a urea synthesis section.

EXAMPLE

Production of methanol, ammonia, and urea from a syngas mixture with the process according to the invention as embodied in the flow scheme of FIG. 1 and described above, is now further elucidated using the standard simulation package Pro-II, taking as boundary condition a maximum input of 5208 kmol/h of oxygen from an ASU to a combined reforming process as described in WO 2008/122399 A1.

In Table 1 the conditions (temperature and pressure) are given for each process step or stream, following the numbering of FIG. 1, as well as the calculated mass balance expressed in kgmol/h (or mtpd).

It can be concluded from this simulation that with the process according to the invention it is feasible to co-produce for example about 8000 mtpd of methanol and about 2000 mtpd of ammonia. The ammonia may be converted into about 3500 mtpd of urea, using the carbon dioxide available within the process.

TABLE 1

| Stream | $H_2$ | CO | $CO_2$ | $CH_4$ | $N_2$ (kgmol/h) | $CH_3OH$ | $NH_3$ | $H_2O$ | Total | T (° C.) | P MPa |
|---|---|---|---|---|---|---|---|---|---|---|---|
| 1 | | | | Natural Gas Feed: 13999 kgmol/h | | | | | | | |
| 2 | 34107.0 | 9603.1 | 4113.5 | 393.2 | 771.6 | | | 157.3 | 49145.7 | 45 | 3 |
| 3 | | | | Air to ASU | | | | | | | |
| 4 | | | | $O_2$ from ASU: 5208 kmol/h (4000 mtpd) | | | | | | | |
| 5 | | | | | 2535.8 | | | | 2535.8 | 45 | 0.1 |
| 6 | | | | Excess $N_2$ and Ar vent from ASU | | | | | | | |
| 7 | 34107.0 | 9603.1 | 4113.5 | 393.2 | 771.6 | | | 94.5 | 49082.9 | 96.3 | 7.8 |
| 8 | 20715.1 | 3303.9 | 3569.9 | 387.4 | 769.1 | 47.2 | | 57.4 | 28850.0 | 51 | 7.2 |
| 9 | 20.7 | 24.0 | 269.9 | 5.8 | 2.5 | 6501.7 | | 510.8 | 7335.4 | 45 | 7.2 |
| 10 | 14717.0 | 2347.2 | 2536.2 | 275.2 | 546.4 | 33.6 | | 40.8 | 20496.4 | 50 | 7.2 |
| 11 | 5998.1 | 956.7 | 1033.7 | 112.2 | 222.7 | 13.7 | | 16.6 | 8353.6 | | |
| 12 | 14682.7 | 2347.2 | 17.9 | 275.2 | 541.1 | | | 23.7 | 17887.8 | 45 | 7.2 |
| 13 | 34.2 | | 2518.4 | | 5.3 | | | 273.0 | 2830.9 | 45 | 0.1 |
| 14 | 14682.7 | 2347.2 | | 275.2 | 541.1 | | | | 17846.2 | 45 | 7.2 |
| 15 | 7856.0 | 79.4 | | | | | | | 7935.4 | 25 | 4.5 |
| 16 | 7617.9 | | | 79.4 | | | | 79.4 | 7776.6 | 97 | 4.4 |
| 17 | 7617.9 | | | 79.4 | 2535.8 | | | 79.4 | 10312.5 | 113 | 4.4 |
| 18 | 7617.9 | | | 79.4 | 2535.8 | | | 79.4 | 10312.5 | 122 | 15.9 |
| 19 | 261.5 | | | 65.0 | 83.7 | | 6.1 | | 416.3 | | |
| 20 | | | | Ammonia: 4893 kgmol/h (2000 mtpd) | | | | | | | |
| 21 | 12824.9 | 3224.5 | 1033.7 | 387.4 | 763.8 | 13.7 | | 16.6 | 18264.6 | 43 | 6.8 |
| 22 | 12824.9 | 3224.5 | 1033.7 | 387.4 | 763.8 | 13.7 | | 16.6 | 18264.6 | 86 | 10 |
| 23 | 4169.0 | 153.5 | 153.7 | 368.8 | 754.9 | 4.9 | | 8.2 | 5613.0 | 49 | 9.5 |
| 24 | 16.4 | 4.1 | 44.8 | 18.6 | 8.8 | 3911.2 | | 893.9 | 4897.8 | 45 | 9.5 |
| 25 | | | | | | | | 1519.0 | 1519.0 | | 4.6 |
| 26 | | | | Methanol: 10403 kgmol/h (8000 mtpd) | | | | | | | |
| 27 | | | | | 2535.8 | | | | 2535.8 | 165 | 4.6 |
| 28 | 34.2 | | 2518.4 | | 5.3 | | | 15.4 | 2573.3 | | |
| 29 | | | | Urea: 2430 kgmol/h (3500 mtpd) | | | | | | | |
| 30 | 6826.7 | 2267.9 | | 275.2 | 541.1 | | | | 9910.9 | 25 | 6.8 |

The invention claimed is:
1. A process for co-producing methanol and ammonia, wherein a syngas mixture consisting essentially of carbon monoxide (CO), carbon dioxide ($CO_2$) and hydrogen ($H_2$) is first partially reacted in a methanol once-through reactor, unreacted syngas is divided into a first and a second stream, the first stream is purified and fed to an ammonia synthesis section, and the second stream is fed to a methanol synthesis and purification section.

2. The process for co-producing methanol and ammonia according to claim 1, comprising
   a) feeding a syngas mixture consisting essentially of CO, $CO_2$ and $H_2$ to a methanol once-through reactor to make a methanol/syngas mixture;
   b) separating the mixture of step a) into crude methanol and unreacted syngas;
   c) dividing the unreacted syngas of step b) into a first and a second stream;
   d) feeding the first stream of step c) to a syngas purification section to make a CO, a $CO_2$ and a $H_2$ stream;
   e) feeding the $H_2$ stream of step d) together with a $N_2$ stream to an ammonia synthesis section to make an ammonia stream;
   f) feeding the second stream of step c) and the CO stream of step d) to a methanol loop reactor to make a methanol-containing mixture;
   g) separating crude methanol from the methanol-containing mixture and recycling the remaining gas to step f); and
   h) feeding the crude methanol from step b) and from step g) to a methanol purification section to result in a methanol stream.

3. The process for co-producing methanol and ammonia according to claim 1, comprising
   a") feeding air to an air separation section to make an $O_2$ and a $N_2$ stream;
   a') reforming a desulphurised hydrocarbon feedstock with $O_2$ from step a") and steam in a combined reforming section to make a syngas mixture consisting essentially of CO, $CO_2$ and $H_2$;
   a) feeding the syngas mixture of step a') to a methanol once-through reactor to make a methanol/syngas mixture;
   b) separating the mixture of step a) into crude methanol and unreacted syngas;
   c) dividing the unreacted syngas of step b) into a first and a second stream;
   d) feeding the first stream of step c) to a syngas purification section to make a CO, a $CO_2$ and a $H_2$ stream;
   e) feeding the $H_2$ stream of step d) together with the $N_2$ stream of step a") to an ammonia synthesis section to make an ammonia stream;
   f) feeding the second stream of step c) and the CO stream of step d) to a methanol loop reactor to make a methanol-containing mixture;
   g) separating crude methanol from the methanol-containing mixture and recycling the remaining gas to step f); and
   h) feeding the crude methanol from step b) and from step g) to a methanol purification section to result in a methanol stream.

4. The process according to claim 1, wherein the syngas mixture has a stoichiometric number SN of from 1.9 to 2.3.

5. The process according to claim 3, wherein a methane-rich feedstock is mixed with steam and passed through an adiabatic pre-reformer (APR), and wherein pre-reformed gas from the APR is divided into three streams that are fed to a steam methane reformer (SMR), a gas heated reformer (GHR), and together with the oxygen to an auto-thermal reformer (ATR), which 3 reforming reactors are operated in parallel.

6. The process according to claim 1, wherein the hydrocarbon feedstock is a methane-rich feedstock that contains as least 75 mol % of methane.

7. The process according to claim 1, wherein the first and the second stream of unreacted syngas are divided in a ratio of from 50/50 to 80/20.

8. The process according to claim 7, wherein the ratio of the first to the second stream is 70/30.

9. The process for co-producing methanol and urea comprising the process of claim 1, and a subsequent step of making urea in a urea synthesis section from the $CO_2$ and $NH_3$ formed in the process.

10. A process for co-producing methanol and ammonia, comprising:
   i) feeding a syngas mixture consisting essentially of CO, $CO_2$ and $H_2$ to a methanol once-through reactor to make a methanol/syngas mixture;
   j) separating the mixture of step i) into crude methanol and unreacted syngas;
   k) dividing the unreacted syngas of step b) into a first and a second stream;
   l) feeding the first stream of step j) to a syngas purification section to make a CO, a $CO_2$ and a $H_2$ stream;
   m) feeding the $H_2$ stream of step k) together with a $N_2$ stream to an ammonia synthesis section to make an ammonia stream;
   n) feeding the second stream of step k) and the CO stream of step 1 to a methanol loop reactor to make a methanol-containing mixture; and
   o) separating crude methanol from the methanol-containing mixture.

11. A process for co-producing methanol and ammonia, comprising:
   a") feeding air to an air separation section to make an $O_2$ and a $N_2$ stream;
   a') reforming a desulphurised hydrocarbon feedstock with $O_2$ from step a") and steam in a combined reforming section to make a syngas mixture consisting essentially of CO, $CO_2$ and $H_2$;
   i) feeding the syngas mixture of step a') to a methanol once-through reactor to make a methanol/syngas mixture;
   j) separating the mixture of step i) into crude methanol and unreacted syngas;
   k) dividing the unreacted syngas of step j) into a first and a second stream;
   l) feeding the first stream of step k) to a syngas purification section to make a CO, a $CO_2$ and a $H_2$ stream;
   m) feeding the $H_2$ stream of step 1 together with the $N_2$ stream of step a") to an ammonia synthesis section to make an ammonia stream;
   n) feeding the second stream of step k and the CO stream of step 1 to a methanol loop reactor to make a methanol-containing mixture; and
   o) separating crude methanol from the methanol-containing mixture.

12. The process of claim 1, wherein syngas conversion to methanol in the once-through methanol reactor is greater than or equal to 45%.

13. The process of claim 10, wherein syngas conversion to methanol in the once-through methanol reactor is greater than or equal to 45%.

14. The process of claim 11, wherein syngas conversion to methanol in the once-through methanol reactor is greater than or equal to 45%.

15. The process of claim 1, wherein about 8000 mtpd of methanol is produced.

16. The process of claim 1, wherein about 2000 mtpd of ammonia is produced.

17. The process of claim 10, wherein about 8000 mtpd of methanol is produced.

18. The process of claim 11, wherein about 8000 mtpd of methanol is produced.

* * * * *